US011926583B2

(12) United States Patent
Saha (10) Patent No.: US 11,926,583 B2
(45) Date of Patent: Mar. 12, 2024

(54) STABILIZED 1, 25-DIHYDROXYVITAMIN D2 AND METHOD OF MAKING SAME

(71) Applicant: CYTOCHROMA INC., Markham (CA)

(72) Inventor: Uttam Saha, Thornhill (CA)

(73) Assignee: EIRGEN PHARMA LTD., Waterford (IE)

( * ) Notice: Subject to any disclaimer, the term of this patent is extended or adjusted under 35 U.S.C. 154(b) by 1795 days.

(21) Appl. No.: 14/146,397

(22) Filed: Jan. 2, 2014

(65) Prior Publication Data

US 2014/0113886 A1 Apr. 24, 2014

Related U.S. Application Data

(63) Continuation of application No. 12/403,271, filed on Mar. 12, 2009, now abandoned.

(60) Provisional application No. 61/036,021, filed on Mar. 12, 2008.

(51) Int. Cl.
*C07C 401/00* (2006.01)
*A61K 31/592* (2006.01)
*A61K 45/06* (2006.01)

(52) U.S. Cl.
CPC .......... *C07C 401/00* (2013.01); *A61K 31/592* (2013.01); *A61K 45/06* (2013.01)

(58) Field of Classification Search
CPC .... A61K 31/592; A61K 45/06; C07C 401/00; A61P 3/02
USPC .......................................... 514/167; 552/653
See application file for complete search history.

(56) References Cited

U.S. PATENT DOCUMENTS

| | | | | |
|---|---|---|---|---|
| 3,880,894 A | * | 4/1975 | De Luca | 552/653 |
| 4,022,891 A | * | 5/1977 | Takeshita | C07J 9/00 514/167 |
| 4,689,180 A | * | 8/1987 | DeLuca | C07C 401/00 514/167 |
| 5,565,442 A | * | 10/1996 | Silver | A61K 9/2013 514/167 |
| 5,786,348 A | * | 7/1998 | Bishop | A61K 31/59 514/167 |
| 6,142,910 A | * | 11/2000 | Heuvelman | A63B 24/00 434/227 |
| 6,242,434 B1 | | 6/2001 | Bishop et al. | |
| 6,362,350 B1 | | 3/2002 | DeLuca et al. | |
| 6,432,936 B1 | | 8/2002 | DeLuca et al. | |
| 6,448,421 B1 | | 9/2002 | Yamauchi | |
| 6,462,031 B2 | | 10/2002 | DeLuca et al. | |
| 6,903,083 B2 | | 6/2005 | Knutson et al. | |
| 8,592,401 B2 | * | 11/2013 | Petkovich | A61K 31/592 514/167 |
| 2005/0148558 A1 | * | 7/2005 | Knutson | C07C 401/00 514/167 |

FOREIGN PATENT DOCUMENTS

| | | |
|---|---|---|
| CN | 1709869 A | 12/2005 |
| EP | 0337305 A1 | 10/1989 |
| JP | H06316558 A | 11/1994 |
| WO | WO-84/04527 | 11/1984 |
| WO | WO-00/43361 | 7/2000 |
| WO | WO-01/02352 | 1/2001 |
| WO | WO-2010/060197 A1 | 6/2010 |

OTHER PUBLICATIONS

A. Kutner at rl. (The Journal of organic Chemistry, 1988, 53, 3457-3465—ACS Publications ; Novel convergent synthesis of side-chain-modified analogs of 1. alpha., 25-dihydroxycholecalciferol and 1. alpha., 25-dihydroxyergocalciferol 1988).*
Office Action, Chinese patent application No. 200980112429.7, dated Dec. 5, 2012.
Extended European Search Report, European patent application No. 09720292.3, dated Mar. 15, 2013.
Baggiolini, E. G., et al., "Stereocontrolled Total Synthesis of 1α,25-Dihydroxycholecalciferol and 1α,25-Dihydroxyergocalciferol," J. Org. Chem., vol. 51, No. 16, pp. 3098-3108 (1986).
Final Office Action, U.S. Appl. No. 12/403,271, dated Jul. 2, 2013.
Final Office Action, U.S. Appl. No. 12/403,271, dated Sep. 6, 2011.
Granja, J.R., et al., "Studies on the Opening of Dioxanone and Acetal Templates and Application to the Synthesis of 1α,25-Dihydroxyvitamin D2," J. Org. Chem., vol. 58, No. 1, pp. 124-131 (1993).
Houghton et al., The case against ergocalciferol (vitamin D2) as a vitamin supplement, Am. J. Clin. Nutr., 84(4):694-7 (2006).
Kutner, A., et al., "Novel Convergent Synthesis of Side-Chain-Modified Analogues of 1α,25-Dihydroxycholecalciferol and 1α,25-Dihydroxyergocalciferol," J. Org. Chem., vol. 53, pp. 3450-3457 (1988).
Nonfinal Office Action, U.S. Appl. No. 12/403,271, dated Apr. 4, 2011.
Nonfinal office action, U.S. Appl. No. 12/403,271, dated Jan. 20, 2012.
Nonfinal office action, U.S. Appl. No. 12/403,271, dated Sep. 21, 2012.
PCT International Search Report for counterpart International Application No. PCT/CA2009/000291, dated Jun. 26, 2009 (5 pages).
PCT Written Opinion for counterpart International Application No. PCT/CA2009/000291, dated Jun. 26, 2009 (5 pages).

(Continued)

*Primary Examiner* — Sarah Pihonak (74) *Attorney, Agent, or Firm* — MARSHALL, GERSTEIN & BORUN LLP (57) ABSTRACT

A stabilized 1,25-dihydroxyvitamin $D_2$ composition which is particularly well suited for pharmaceutical formulations, pharmaceutical formulations of the 1,25-dihydroxyvitamin $D_2$ composition, and a method of making the purified composition by purifying a crude 1,25-dihydroxyvitamin $D_2$ from acetone/water, are disclosed.

19 Claims, 1 Drawing Sheet

(56) References Cited

OTHER PUBLICATIONS

Sicinski, R. R., et al., "Synthesis of 1α, 25-Dihydroxyvitamin D2, Its 24 Epimer and Related Isomers, and Their Binding Affinity for the 1,25-Dihydroxyvitamin D3 Receptor," Bioorganic Chemistry, 13, pp. 158-169 (1985).

Tomkins et al., Determination of vitamin D 2 in gelatin-protected vitamin A acetate-vitamin D2 beadlets by high pressure liquid chromatography, Anal. Chem., 46(11):1602-4 (1974).

Tsuji, M., et al., "A New and Convenient Synthesis of 1α, 25-Dihydroxyvitamin D2 and Its 24R-Epimer," Bull. Chem. Soc. Jpn., vol. 62, No. 10, pp. 3132-3137 (1989).

Zhang, F., et al., "Degradation Chemistry of a Vitamin D Analogue (Ecalcidene) Investigated by HPLC-MS, HPLC-NMR and Chemical Derivatization," J. Pharm. Biomed. Anal., vol. 40, pp. 850-863 (2006).

El-Khoury, et al., "Stability of 1,25-dihydroxyvitamin $D_2$ and 1,25-dihydroxyvitamin $D_3$ in human serum," CLB-07967, 4C (Jan. 17, 2012).

Lips, P., Review: Relative Value of 25 (OH)D and 1,25 $(OH)_2D$ Measurements, Journal of Bone and Mineral Research, vol. 22, N. 11 (2007).

Sitrin et al., Comparison of vitamin D and 25-hydroxyvitamin D absorption in the rat, Am. J. Physiol., 242(4):G326-32 (1982).

Holmberg et al., Absorption of a pharmacological dose of vitamin D3 from two different lipid vehicles in man: comparison of peanut oil and a medium chain triglyceride, Biopharm. Drug Dispos., 11(9):807-15 (1990).

International Council for Harmonisation of Technical Requirements for Pharmaceuticals for Human Use (ICH) Guidance for Industry, Q3C Impurities: Residual Solvents (ICH Q3C), Dec. 1997.

International Council for Harmonisation of Technical Requirements for Pharmaceuticals for Human Use (ICH) Guidance for Industry, Q3C Tables and List, Revision 4, Aug. 2018.

United States Pharmacopeia, the National Formulary, SP 30 <467> Residual Solvents (dated Mar. 23, 2007).

\* cited by examiner

STABILIZED 1, 25-DIHYDROXYVITAMIN D2 AND METHOD OF MAKING SAME

CROSS-REFERENCE TO RELATED APPLICATIONS

This is a continuation of U.S. patent application Ser. No. 12/403,271, filed Mar. 12, 2009, which claims the benefit under 35 U.S.C. § 119(e) of U.S. Provisional Patent Application Ser. No. 61/036,021 filed on Mar. 12, 2008. The disclosure of each priority reference is incorporated herein by reference.

BACKGROUND

1. Field of the Disclosure

The disclosure relates generally to active vitamin D hormones in purified form. More particularly, the disclosure relates to stabilized 1,25-dihydroxyvitamin $D_2$ which is particularly well suited for pharmaceutical formulations.

2. Brief Description of Related Technology

Vitamin D compounds having a hydroxy group at the 1-α position, often considered to be activated vitamin D compounds, have had considerable attention in recent years because of their potent activities. These activated vitamin D compounds are, however, also known as being chemically unstable, particularly under exposure to light and to oxygen, and as having poor storage stability at higher temperatures. The compounding of activated vitamin D compounds into pharmaceutical formulations can exacerbate these stability problems.

U.S. Pat. No. 6,903,083 (Jun. 7, 2005) reported purifying 24-hydroxyvitamin $D_2$ and cis-1α-hydroxyvitamin $D_2$ by recrystallization from methyl formate, and results of stability testing thereof.

SUMMARY

One aspect of the disclosure provides a surprisingly stable 1,25-dihydroxyvitamin $D_2$, characterized by being free of methyl formate, preferably completely free of methyl formate.

Another aspect of the disclosure provides an efficient method for crystallizing 1,25-dihydroxyvitamin $D_2$ to produce a stabilized 1,25-dihydroxyvitamin $D_2$ at relatively high yield, the method including crystallization from an acetone/water mixture.

For the compositions and methods described herein, preferred features, such as components, compositional ranges thereof, functional properties, substituents, conditions, and steps, can be selected from the various examples provided herein.

Further aspects and advantages will be apparent to those of ordinary skill in the art from a review of the following detailed description, taken in conjunction with the drawings. While the composition and method are susceptible of embodiments in various forms, the description hereafter includes specific embodiments with the understanding that the disclosure is illustrative, and is not intended to limit the invention to the specific embodiments described herein.

BRIEF DESCRIPTION OF THE DRAWINGS

For further facilitating the understanding of the present invention, two drawing figures are appended hereto.

DETAILED DESCRIPTION

The stabilized 1,25-dihydroxyvitamin $D_2$ is characterized by being free of methyl formate and having a high level of purity (e.g. at least 97%). The method for preparing the stabilized 1,25-dihydroxyvitamin $D_2$ can include crystallization from an acetone/water mixture.

The stabilized 1,25-dihydroxyvitamin $D_2$ is and method of crystallization are contemplated to encompass embodiments including any combination of one or more of the additional optional elements, features and steps further described below (including those shown in the figures) unless stated otherwise.

The stabilized 1,25-dihydroxyvitamin $D_2$ is crystalline, storage stable and well suited for modern therapy formulations. Studies have demonstrated that stabilized 1,25-dihydroxyvitamin $D_2$ according to the description herein is surprisingly stable. In particular, it is characterized by a reduced rate of degradation on heat challenge and during prolonged storage. The stabilized 1,25-dihydroxyvitamin $D_2$ according to the description herein will exhibit excellent, unprecedented storage stability when formulated in a pharmaceutical dosage form, e.g., a soft gelatin capsule.

The stabilized 1,25-dihydroxyvitamin $D_2$ has a purity equal to or greater than 97% (i.e., at least 97%) based on total area under the curve (AUC) by high performance liquid chromatography (HPLC), preferably at least 98% purity or at least 98.5% purity. It is also free of methyl formate. The stabilized 1,25-dihydroxyvitamin $D_2$ substance optionally has a low concentration of 1,25-dihydroxyprevitamin $D_2$ (e.g. preferably not more than 2.5%, not more than 1%, or not more than 0.5%).

Methyl formate is taught in the prior art as a suitable crystallization solvent for 1,25-dihydroxyvitamin $D_2$ and many other active vitamin D compounds. It has now been found that residual methyl formate has a deleterious effect on stability of 1,25-dihydroxyvitamin $D_2$ and its previtamin, leading to marked degradation over time, even at very low levels of residual methyl formate concentration and under controlled storage conditions (e.g. −20° C. and inert atmosphere). Without intending to be bound by any particular theory, it is believed that methyl formate hydrolyzes (e.g., at elevated temperature, or over time), in the presence of even a very small amount of water, to produce formic acid and methanol. Further without intending to be bound by any particular theory, it is believed that formic acid promotes the formation of 1,25-dihydroxyvitamin $D_2$ by-products presumably by causing the formation of a conjugated diene via protonation of the 25-hydroxy group and subsequent removal of water.

Accordingly, in another aspect the stabilized 1,25-dihydroxyvitamin $D_2$ will optionally be further free of or substantially free of residual solvents which can produce acids including, but not limited to, alcohol esters of organic acids and alcohol esters of inorganic esters. Nonlimiting examples include formate esters (e.g., methyl formate, ethyl formate); acetate esters (e.g., methyl acetate, butyl acetate, ethyl acetate, isoamyl acetate, 1,2-ethanediol diacetate, 1,2,3-propanetriol triacetate) and lactate esters (e.g., ethyl lactate, methyl lactate). For example, the level of such residual components is preferably less than 1%, 0.5%, 1000 ppm, 500 ppm, or 100 ppm. The stabilized 1,25-dihydroxyvitamin $D_2$ is also optionally free of or substantially free of one or more of the following: halogenated solvents, dimethylsulfoxide, dimethylformamide, and acids. For example, the level of such residual halogenated solvents is preferably less than 1%, 0.5%, 1000 ppm, 500 ppm, or 100 ppm.

Further optionally, but preferably, the stabilized 1,25-dihydroxyvitamin $D_2$ according to the description herein has a purity of at least 97% (or at least 98% or at least 98.5%), a residual solvents content of 0.5% or less, further optionally a total impurities content of 1.5% or less, and further optionally has no single impurity greater than 0.5% by HPLC.

The stabilized 1,25-dihydroxyvitamin $D_2$ according to the description herein is stable under conditions of heat challenge. In one embodiment, the 1,25-dihydroxyvitamin $D_2$ is at least about 98%, preferably at least 98.5%, for example at least 99% pure after storage at 60° C. for at least 24 hours, preferably for at least 72 hours. In another embodiment, the amount of 1,25-dihydroxyvitamin $D_2$ that remains after storage at 60° C. for at least 24 hours preferably is at least 97.5%, more preferably at least 99%, for example at least 99.9% of the initial amount. In another embodiment, the amount of 1,25-dihydroxyvitamin $D_2$ that remains after storage at 60° C. for at least 72 hours preferably is at least 97%, more preferably at least 98.5%, for example at least about 99.5% of the initial amount.

The stabilized 1,25-dihydroxyvitamin $D_2$ according to the description herein is stable over a prolonged period of time at long term storage conditions. In one embodiment, the stabilized 1,25-dihydroxyvitamin $D_2$ according to the description herein has a purity of at least 98%, preferably at least 98.5%, more preferably at least 99% after storage at −20° C. under argon for at least 3, 6, 9, 12, or 15 months. Embodiments and examples of the percentage of the initial amount of 1,25-dihydroxyvitamin $D_2$ that remains after storage at −20° C. under argon for at least 3, 6, 9, 12, or 15 months are shown in Table 1.

TABLE 1

| Period of Time | Percentage of the initial amount of 1,25-dihydroxyvitamin $D_2$ that remains after a prolonged period of time | | |
|---|---|---|---|
| | Preferably | More preferably | Example |
| At least 3 months | At least 99% | At least 99.5% | At least 99.9% |
| At least 6 months | At least 97% | At least 98.5% | At least 99.9% |
| At least 9 months | At least 94% | At least 97% | At least 99.9% |
| At least 12 months | At least 94% | At least 97% | At least 99.9% |
| At least 15 months | At least 94% | At least 97% | At least 99.9% |

The stabilized 1,25-dihydroxyvitamin $D_2$ is suitably used in pharmaceutical formulations, such as for oral use (e.g., soft or hard gelatin capsules, solutions, tablets) and for parenteral use. Thus, the pharmaceutical formulation made from or containing stabilized 1,25-dihydroxyvitamin $D_2$ can be in the form of a non-aqueous solution or a non-aqueous suspension (e.g. contained in a vial or ampoule) or in solid form. In one preferred embodiment, the stabilized 1,25-dihydroxyvitamin $D_2$ formulation is in an oil (e.g. fractionated coconut oil). In another preferred embodiment, the stabilized 1,25-dihydroxyvitamin $D_2$ formulation is a solid in the form of a tablet, a capsule, a granule, or a powder. The pharmaceutical formulation can comprise, consist essentially of, or consist of stabilized 1,25-dihydroxyvitamin $D_2$ together with one or more pharmaceutically acceptable excipients. Pharmaceutically acceptable excipients include functional and non-functional ingredients including carriers, diluents, processing aids, and release-modifying agents. Such pharmaceutical formulations can be made with the stabilized 1,25-dihydroxyvitamin $D_2$ substance described herein, using any suitable technique including known techniques.

The dosage of 1,25-dihydroxyvitamin $D_2$ for oral or parenteral administration generally is about 0.1 μg per week to 100 μg per week, preferably about 0.7 μg per week to about 70 μg per week, which can be split into daily or other periodic doses, such as three times per week for administration concomitant with hemodialysis. In exemplary embodiments, a parenteral dosage equivalent to about 0.5 μg per day to about 7 μg per day is contemplated, while an oral dosage equivalent to about 0.1, 0.5, 1, 2, 3, 4, 5, 6, 7, 8, 9, or 10 μg per day is contemplated.

The stabilized 1,25-dihydroxyvitamin $D_2$ can be dispensed by unit dosage form comprising about 0.1 μg to about 25 μg in a pharmaceutically acceptable carrier per unit dosage, for example about 1 μg to about 10 μg or about 1 μg to about 5 μg. A sustained-release or delayed, sustained-release unit dosage form, including about 1 μg to about 10 μg, or more preferred about 3 μg to about 5 μg, for example, is also contemplated.

For example, in a soft gelatin formulation, the capsule fill suitably contains stabilized 1,25-dihydroxyvitamin $D_2$ which preferably is dissolved in a pharmaceutically acceptable oil, e.g., fractionated coconut oil, and includes an antioxidant which may be, for example, butylated hydroxyanisole (BHA), butylated hydroxytoluene (BHT) or vitamin E. The capsule shell preferably contains gelatin, glycerin, titanium dioxide and coloring agent. The fill is typically about 30-90% by weight of the whole capsule, preferably about 40-70% by weight.

The 1,25-dihydroxyvitamin $D_2$ compound may be prepared by any of the known methods of synthesis. Crude 1,25-dihydroxyvitamin $D_2$ can be column purified to remove the trans isomer according to known methods. A column-purified 1,25-dihydroxyvitamin $D_2$ can be stabilized by recrystallization from a suitable organic solvent or mixture of organic solvent and water consistent with the disclosure herein, e.g., acetone and water. The recrystallized crystals are then preferably ground to a fine powder and dried in a vacuum oven (e.g. at 40° C. for 8-12 hours) to remove residual solvents. One or more successive (generally at least two) recrystallizations can be performed. Suitable solvents, in addition to acetone/water, include acetonitrile, butanol, diethyl ketone, ethanol, ether, ethylene glycol, heptane, methanol, methyl ethyl ketone, propanol, tetrahydrofuran, water, and combinations thereof. If recrystallizations are performed from acid-containing or acid-yielding solvents such as methyl formate, then one or more successive (generally at least two) recrystallizations will be performed with a preferred solvent according to the disclosure herein, to remove undesired residual components.

Partially pure 1,25-dihydroxyvitamin $D_2$ preferably is crystallized from a solvent that is free of methyl formate, preferably further free of at least one of the following solvents selected from the group consisting of formate ester solvents, acetate ester solvents, lactate ester solvents, alcohol ester solvents, halogenated solvents, dimethylsulfoxide, dimethylformamide, and solvents capable of generating acid. The solvent system is preferably acetone/water, more preferably using a 1:1 ratio. While other solvents may be used, it was found that crystallization from acetone/water gave a very high yield of desired product and also beneficially provided very low levels of 1,25-dihydroxyprevitamin $D_2$. Each acetone/water crystallization step was found to give greater than 90% yield compared to methyl formate crystallization which was found to give yields in the range of 50% to 60%.

If a multi-stage crystallization method is performed to purify the 1,25-dihydroxyvitamin $D_2$, then preferably the preferred solvents identified herein (e.g., free of methyl formate, preferably further free of at least one of the following solvents selected from the group consisting of formate ester solvents, acetate ester solvents, lactate ester solvents, alcohol ester solvents, halogenated solvents, dimethylsulfoxide, dimethylformamide, and solvents capable of generating acid) are used in the final crystallization stage, with the goal of minimizing and preferably at least substantially eliminating non-desired species identified herein, such as residual solvents.

The crude material is first refluxed with acetone at a temperature in a range of 50° C. to 60° C. (15 ml/1 g) until a clear solution is obtained. The solution is then filtered through a sintered funnel and a volume of water (preferably an equal volume) is gradually added. Once the temperature is reduced to about 25° C. degrees and crystallization begins, the mixture is further chilled (e.g. flask placed at 4° C. freezer for 24 h). The solid is then filtered and washed, preferably with an acetone/water mixture (e.g. 1:1 ratio). Preferably, the acetone/water mixture is pre-chilled, e.g. to 4° C. The crystallization can be repeated until the product meets the desired purity specifications, preferably to a level of at least 97% purity, more preferably at least 98% or at least 98.5% purity by HPLC.

The HPLC analysis can suitably follow the parameters in Table 2 below.

TABLE 2

| Column: | YMC-Pack Pro C18, 5 μm, 12 nm, 250 × 4.6 mm |
|---|---|
| Mobile phase: | 70:30 acetonitrile:water isocratic |
| Flow rate: | 1.5 ml per minute |
| Wave length: | 265 nm |
| Run time: | 20 min |
| Sample temp: | 15° C. ± 5° C. |
| Column temp: | 30° C. ± 5° C. |
| Sample concentration: | 1 mg/ml |
| Injection volume: | 10 μL |

EXAMPLES

The following examples are provided for illustration and are not intended to limit the scope of the invention.

Example 1

Preparation of Stabilized 1,25-Dihydroxyvitamin $D_2$ 1,25-dihydroxyvitamin $D_2$ is prepared following the procedure described in the Journal of Organic Chemistry 1988, 53, 3450-3457. The crude material is treated with maleic anhydride in tetrahydrofuran at room temperature, followed by column purification, to remove the trans isomer via a Diels Alder adduct.

Partially pure 1,25-dihydroxyvitamin $D_2$ was crystallized from acetone/water (1:1). The crude material was first refluxed with HPLC grade acetone (15 ml/1 g) until a clear solution was obtained. It was then filtered and an equal volume of 18.2 megaohm water was gradually added. Once the temperature came down to about 25° C. degrees and crystal formation started, the flask was placed in a 4° C. freezer for 24 h. The solid was filtered and washed with pre-chilled 1:1 acetone/water at 4° C. The crystallization was repeated until the product met the desired purity specifications. In this example, the purity was 99.4% (HPLC); single known impurity not more than 0.5% (1β,25-dihydroxyvitamin $D_2$, 5,6-trans-1,25-dihydroxyvitamin $D_2$, 22-cis-1,25-dihydroxyvitamin $D_2$, and 1,25-dihydroxyprevitamin $D_2$); single unknown impurity not more than 0.1%. To dry, the solid material was ground via a mortar and pestle and placed at 40° C. under vacuum for 8-12 hours.

The parameters in Table 1 above were used for the HPLC analysis.

Example 2

Accelerated Stability Testing of Stabilized 1,25-Dihydroxyvitamin $D_2$

Figure 1:
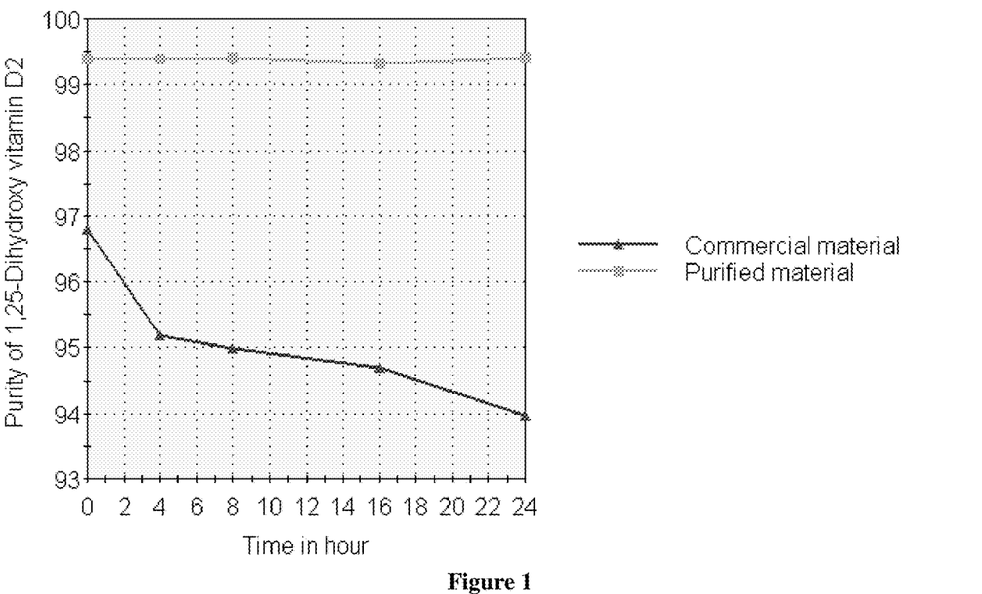
FIGS. 1 and 2 depict accelerated stability testing of stabilized 1,25-dihydroxyvitamin $D_2$ according to the disclosure herein compared to 1,25-dihydroxyvitamin $D_2$ containing methyl formate.
Figure 2:
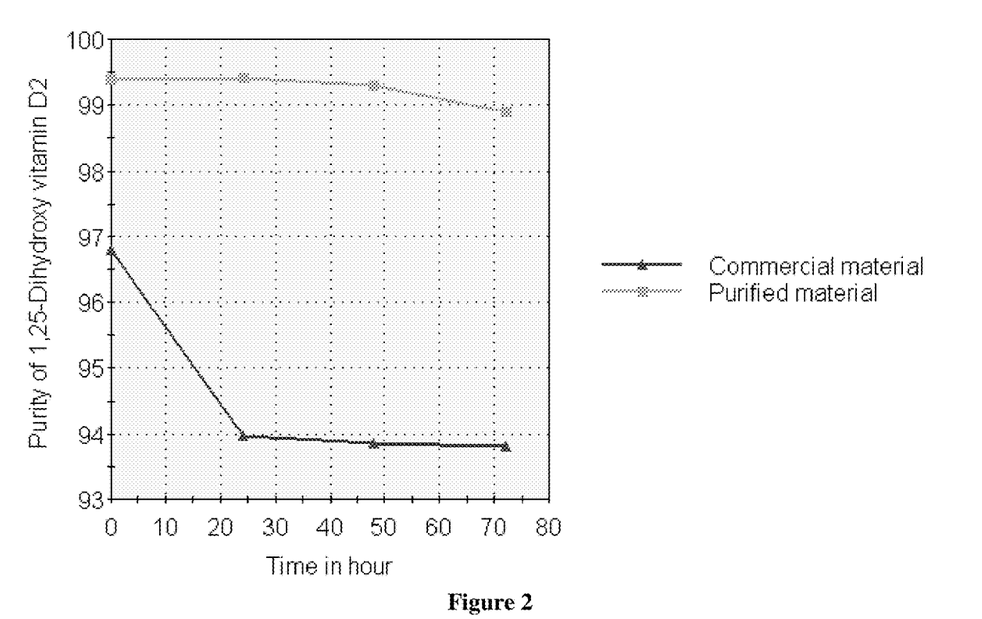

Samples of stabilized 1,25-dihydroxyvitamin $D_2$ according to Example 1 and commercially-obtained 1,25-dihydroxyvitamin $D_2$ (SAFC, Madison, Wis. USA) made by crystallization from methyl formate were placed in a 60° C. oven in several 2 ml amber vials with Teflon-lined caps. Samples were taken out at different time points and purity was checked by HPLC according to Example 1. The results are presented in Tables 3 and 4 below and in FIGS. 1 and 2. FIG. 1 shows the observed stability of the two preparations over the 24 hours, and FIG. 2 shows stability over 72 hours. From these studies it is clear that the purified material prepared according to Example 1 was surprisingly more stable compared to the commercially available material prepared using methyl formate and containing residual methyl formate. The stabilized material prepared according to the Example 1 will clearly have advantage when any heat is required during formulation.

TABLE 3

|  | methyl formate | At 60° C. | 0 h | 4 h | 8 h | 16 h | 24 h | 48 h | 72 h |
|---|---|---|---|---|---|---|---|---|---|
| Commercial | 500 ppm | Purity | 96.80 | 95.18 | 94.98 | 94.69 | 93.98 | 93.86 | 93.82 |
| Example 1 | not detected | (absolute %) | 99.40 | 99.38 | 99.42 | 99.33 | 99.42 | 99.31 | 98.89 |

TABLE 4

|  | methyl formate | At 60° C. | Initial % | 4 h | 8 h | 16 h | 24 h | 48 h | 72 h |
|---|---|---|---|---|---|---|---|---|---|
| Commercial | 500 ppm | Purity | 100 | 98.33 | 98.12 | 97.82 | 97.09 | 96.97 | 96.92 |
| Example 1 | not detected | (% of initial amount) | 100 | 99.98 | 100 | 99.93 | 100 | 99.90 | 99.50 |

Example 3

Long-Term Stability Testing of Stabilized 1,25-Dihydroxyvitamin $D_2$

Additional samples of 1,25-dihydroxyvitamin $D_2$ (SAFC, Madison, Wis. USA) that were substantially free of 1,25-dihydroxyprevitamin $D_2$ were made by crystallization from methyl formate and having varying levels of residual methyl formate. These samples were stored at −20° C. under argon and periodically tested for purity by HPLC. Other samples of 1,25-dihydroxyvitamin $D_2$ made according to the disclosure herein and without methyl formate were also made and tested under the same conditions. The results are shown in Tables 5 and 6 below.

TABLE 5

| Batch | 1,25-dihydroxyvitamin $D_2$ | Purity of 1,25-Dihydroxyvitamin $D_2$ (absolute %) | | | | | |
|---|---|---|---|---|---|---|---|
| | | 0 months | 3 months | 6 months | 9 months | 12 months | 15 months |
| A | 10 ppm methyl formate, 0.11% 1,25-dihydroxyprevitamin $D_2$ | 99.48% | 97.99% (3½M) | | | | |
| B | 16 ppm methyl formate, no 1,25-dihydroxyprevitamin $D_2$ | 99.8% | | | | 93.76% (11M) | |
| C | 78 ppm methyl formate, 0.04% 1,25-dihydroxyprevitamin $D_2$ | 97.54% | | 94.3% (7M) | | | |
| D | 4061 ppm methyl formate, 0.21% 1,25-dihydroxyprevitamin $D_2$ | 95.55% | 94.36% | | 80.98% | | |
| E | no methyl formate, no 1,25-dihydroxyprevitamin | 97.7% | | 97.7% | | | |
| F | no methyl formate, 2% 1,25-dihydroxyprevitamin $D_2$ | 99.5% | 99.5% | | | 98.7% | |
| G | no methyl formate, no 1,25-dihydroxyprevitamin | 99.36% | | | 99.42% | | 99.40% |
| H | no methyl formate, no 1,25-dihydroxyprevitamin | 99.40% | | 99.4% | | 99.39% | |

TABLE 6

| Batch | 1,25-dihydroxyvitamin $D_2$ | Purity of 1,25-Dihydroxyvitamin $D_2$ (% of the initial amount) | | | | | |
|---|---|---|---|---|---|---|---|
| | | Initial % | 3 months | 6 months | 9 months | 12 months | 15 months |
| A | 10 ppm methyl formate, 0.11% 1,25-dihydroxyprevitamin $D_2$ | 100% | 98.50% (3½M) | | | | |
| B | 16 ppm methyl formate, no 1,25-dihydroxyprevitamin $D_2$ | 100% | | | | 93.95% (11M) | |
| C | 78 ppm methyl formate, 0.04% 1,25-dihydroxyprevitamin $D_2$ | 100% | | 96.68% (7M) | | | |
| D | 4061 ppm methyl formate, 0.21% 1,25-dihydroxyprevitamin $D_2$ | 100% | 98.75% | | 84.75% | | |
| E | no methyl formate, no 1,25-dihydroxyprevitamin | 100% | | 100% | | | |
| F | no methyl formate, 2% 1,25-dihydroxyprevitamin $D_2$ | 100% | 100% | | | 99.2% | |
| G | no methyl formate, no 1,25-dihydroxyprevitamin | 100% | | | 100% | | 100% |
| H | no methyl formate, no 1,25-dihydroxyprevitamin | 100% | | 100% | | 100% | |

Besides the exceptions noted at 3½ months, 7 months, and 11 months, the samples were tested at zero, 3 months, 6 months, 9 months, 12 months, and 15 months after manufacture. Quite surprisingly, samples exceeding 99% purity at the time of manufacture, and even having low amounts of 1,25-dihydroxyprevitamin $D_2$ (e.g., 0.11% or 0%) but containing even a small amount of residual methyl formate (e.g., 10 ppm or 16 ppm) were found to fall below 98% purity within 3½ months and below 94% purity by 11 months. In contrast, 1,25-dihydroxyvitamin $D_2$ prepared according to the invention crystallized from acetone/water and containing no methyl formate (batches G & H described above) showed absolutely no decrease in purity over at least fifteen months of storage.

A list of specific, non-exclusive aspects of the invention are described in the paragraphs that follow.

A stabilized 1,25-dihydroxyvitamin $D_2$ composition, characterized by a purity of at least 97% based on total AUC by an HPLC assay and being free of methyl formate.

The stabilized 1,25-dihydroxyvitamin $D_2$ composition according to paragraph [0037], wherein the purity is at least 98%, preferably at least 98.5%.

The stabilized 1,25-dihydroxyvitamin $D_2$ composition according to paragraph [0037], wherein the amount of 1,25-dihydroxyprevitamin $D_2$ is 2.5% or less, preferably 1.0% or less, more preferably 0.5% or less based on the total weight of the 1,25-dihydroxyvitamin $D_2$.

The stabilized 1,25-dihydroxyvitamin $D_2$ composition according to any one of the preceding paragraphs, being free of acids.

The stabilized 1,25-dihydroxyvitamin $D_2$ composition according to any one of the preceding paragraphs, wherein the amount of total residual solvent is 1.0% or less, preferably 0.5% or less.

The stabilized 1,25-dihydroxyvitamin $D_2$ composition according to any one of the preceding paragraphs, being substantially free of formate ester solvents.

The stabilized 1,25-dihydroxyvitamin $D_2$ composition according to any one of the preceding paragraphs, being substantially free of acetate ester solvents.

The stabilized 1,25-dihydroxyvitamin $D_2$ composition according to any one of the preceding paragraphs, being substantially free of lactate ester solvents.

The stabilized 1,25-dihydroxyvitamin $D_2$ composition according to any one of the preceding paragraphs, being substantially free of alcohol ester solvents.

The stabilized 1,25-dihydroxyvitamin $D_2$ composition according to any one of the preceding paragraphs, being substantially free of halogenated solvents, dimethylsulfoxide, and dimethylformamide.

The stabilized 1,25-dihydroxyvitamin $D_2$ composition according to any one of the preceding paragraphs, being substantially free of solvents capable of generating acid at elevated temperature or over time.

The stabilized 1,25-dihydroxyvitamin $D_2$ composition according to any one of the preceding paragraphs, wherein the purity is at least 98%, preferably at least 98.5%, more preferably at least 99% after the composition is stored at about 60° C. for a period of at least 24 hours, preferably at least 72 hours.

The stabilized 1,25-dihydroxyvitamin $D_2$ composition according to any one of the preceding paragraphs, wherein at least about 97.5%, preferably at least 99%, more preferably at least 99.5% of the initial amount of the 1,25-dihydroxyvitamin $D_2$ remains after the composition is stored at about 60° C. for a period of at least 24 hours, preferably for at least 72 hours.

The stabilized 1,25-dihydroxyvitamin $D_2$ composition according to any one of the preceding paragraphs, wherein the purity is at least about 98%, preferably at least 98.5%, more preferably at least 99% after the composition is stored at about −20° C. under argon for a period of at least 6 months.

The stabilized 1,25-dihydroxyvitamin $D_2$ composition according to any one of the preceding paragraphs, wherein at least about 97%, preferably at least 98.5%, more preferably at least 99.9% of the initial amount of the 1,25-dihydroxyvitamin $D_2$ remains after the composition is stored at about −20° C. under argon for a period of at least 6 months.

The stabilized 1,25-dihydroxyvitamin $D_2$ composition according to any one of the preceding paragraphs, wherein the purity is at least about 98%, preferably at least 98.5%, more preferably at least 99% after the composition is stored at about −20° C. under argon for a period of at least 9 months.

The stabilized 1,25-dihydroxyvitamin $D_2$ composition according to any one of the preceding paragraphs, wherein at least about 94%, preferably at least 97%, more preferably at least 99.9% of the initial amount of the 1,25-dihydroxyvitamin $D_2$ remains after the composition is stored at about −20° C. under argon for a period of at least 9 months.

The stabilized 1,25-dihydroxyvitamin $D_2$ composition according to any one of the preceding paragraphs, wherein the purity is at least about 98%, preferably at least 98.5%, more preferably at least 99% after the composition is stored at about −20° C. under argon for a period of at least 12 months.

The stabilized 1,25-dihydroxyvitamin $D_2$ composition according to any one of the preceding paragraphs, wherein at least about 94%, preferably at least 98%, more preferably at least 99.9% of the initial amount of the 1,25-dihydroxyvitamin $D_2$ remains after the composition is stored at about −20° C. under argon for a period of at least 12 months.

A pharmaceutical composition comprising an active component which is the stabilized 1,25-dihydroxyvitamin $D_2$ composition of any one of paragraphs [0037] to [0055] and a pharmaceutically acceptable excipient.

The composition of paragraph [0056], which is a tablet.

The composition of paragraph [0056], which is a soft gelatin capsule.

The composition of paragraph [0056], which is a non-aqueous solution or a non-aqueous suspension.

The composition of paragraph [0059], wherein the non-aqueous solution or the non-aqueous suspension is contained in a vial.

The composition of paragraph [0059], wherein the non-aqueous solution or the non-aqueous suspension is contained in an ampoule.

The composition of paragraph [0056], in unit dosage form, having a content of active component of 0.1 µg to 25 µg.

The composition of paragraph [0056], comprising a solution of an effective amount of the stabilized 1,25-dihydroxyvitamin $D_2$ in an oil, the solution contained in a soft gelatin capsule.

The composition of paragraph [0063], wherein the oil comprises fractionated coconut oil.

The composition of paragraph [0063], the oil solution further comprising an antioxidant.

The composition of paragraph [0065], wherein the antioxidant is selected from the group consisting of butylated hydroxyanisole (BHA), butylated hydroxytoluene (BHT) or vitamin E.

The composition of paragraph [0066], wherein the antioxidant is butylated hydroxyanisole (BHA).

The composition of paragraph [0066], wherein the antioxidant is butylated hydroxytoluene (BHT).

The composition of paragraph [0066], wherein the antioxidant is vitamin E.

The composition of paragraph [0056], comprising a solid pharmaceutical preparation of an effective amount of the stabilized 1,25-dihydroxyvitamin D2 composition, wherein the solid pharmaceutical preparation is in the form of a tablet, a capsule, a granule or a powder.

The composition of paragraph [0070], wherein the pharmaceutical preparation is in the form of a tablet.

The composition of paragraph [0070], wherein the pharmaceutical preparation is in the form of a capsule.

The composition of paragraph [0070], wherein the pharmaceutical preparation is in the form of a granule.

The composition of paragraph [0070], wherein the pharmaceutical preparation is in the form of a powder.

A method for purifying crude 1,25-dihydroxyvitamin $D_2$, comprising crystallizing 1,25-dihydroxyvitamin $D_2$ from a solvent system free of methyl formate.

The method of paragraph [0075], wherein the solvent system is further free of at least one of the following solvents selected from the group consisting of formate ester solvents, acetate ester solvents, lactate ester solvents, alcohol ester solvents, halogenated solvents, dimethylsulfoxide, dimethylformamide, and solvents capable of generating acid.

The method of paragraph [0076], wherein the solvent system is free of formate ester solvents, acetate ester solvents, lactate ester solvents, alcohol ester solvents, halogenated solvents, dimethylsulfoxide, dimethylformamide, and solvents capable of generating acid.

The method of any one of paragraphs [0075] to [0077], comprising performing said crystallization as the final crystallization stage in a multi-stage crystallization purification.

The method of any one of paragraphs [0075] to [0078], wherein the solvent system is an acetone/water mixture.

The method of paragraph [0079], wherein the acetone/water mixture is HPLC grade.

The method of paragraph [0079] or [0080], wherein the acetone/water mixture is 40-60% water by volume.

The method of paragraph [0081], wherein the acetone/water mixture is about 50% water by volume.

The method according to any one of paragraphs [0079] to [0082], comprising
  refluxing crude 1,25-dihydroxyvitamin $D_2$ with HPLC grade acetone;
  filtering off solids;
  adding a volume of 18.2 megaohm water to the acetone solution; and
  reducing the temperature of the solution to crystallize 1,25-dihydroxyvitamin $D_2$.

The method according to any one of paragraphs [0079] to [0083], further comprising washing the crystallized 1,25-dihydroxyvitamin $D_2$ with an acetone/water solution.

The method according to any one of paragraphs [0079] to [0084], further comprising drying the crystallized 1,25-dihydroxyvitamin $D_2$ to remove residual solvents.

The method according to any one of paragraphs [0079] to [0085], further comprising treating crude 1,25-dihydroxyvitamin $D_2$ with maleic anhydride to remove the 5,6-trans isomer of 1,25-dihydroxyvitamin $D_2$, if present, via a Diels Alder adduct, prior to crystallization.

A stabilized 1,25-dihydroxyvitamin $D_2$ composition, characterized by a purity of at least 97% based on total AUC by an HPLC assay and being free of methyl formate.

The stabilized 1,25-dihydroxyvitamin $D_2$ composition according to paragraph [0087], comprising 2.5% by weight or less of 1,25-dihydroxyprevitamin $D_2$ based on the total weight of the 1,25-dihydroxyvitamin $D_2$.

The stabilized 1,25-dihydroxyvitamin $D_2$ composition according to paragraph [0087], wherein the amount of total residual solvent is 1.0% or less.

The stabilized 1,25-dihydroxyvitamin $D_2$ composition according to paragraph [0087], being free of acids and substantially free of at least one of the following solvents selected from the group consisting of formate ester solvents, acetate ester solvents, lactate ester solvents, alcohol ester solvents, halogenated solvents, dimethylsulfoxide, dimethylformamide, and solvents capable of generating acid at elevated temperature or over time.

The stabilized 1,25-dihydroxyvitamin $D_2$ composition according to paragraph [0087], wherein the purity is at least 98 after the composition is stored at about 60° C. for a period of at least 24 hours.

The stabilized 1,25-dihydroxyvitamin $D_2$ composition according to paragraph [0087], wherein at least about 97.5% of the initial amount of the 1,25-dihydroxyvitamin $D_2$ remains after the composition is stored at about 60° C. for a period of at least 24 hours.

The stabilized 1,25-dihydroxyvitamin $D_2$ composition according to paragraph [0087], wherein the purity is at least about 98%, after the composition is stored at about −20° C. under argon for a period of at least 6 months.

The stabilized 1,25-dihydroxyvitamin $D_2$ composition according to paragraph [0087], wherein at least about 97% of the initial amount of the 1,25-dihydroxyvitamin $D_2$ remains after the composition is stored at about −20° C. under argon for a period of at least 6 months.

The stabilized 1,25-dihydroxyvitamin $D_2$ composition according to paragraph [0087], wherein the purity is at least about 98% after the composition is stored at about −20° C. under argon for a period of at least 12 months.

A pharmaceutical composition comprising an active component which is the stabilized 1,25-dihydroxyvitamin $D_2$ composition of paragraph [0087] and a pharmaceutically acceptable excipient.

The composition of paragraph [0096], which is selected from the group consisting of a tablet, a soft gelatin capsule, a non-aqueous solution, and a non-aqueous suspension.

The composition of paragraph [0096], in unit dosage form, having a content of active component of 0.1 µg to 25 µg.

The composition of paragraph [0097], comprising a solution of an effective amount of the stabilized 1,25-dihydroxyvitamin $D_2$ in fractionated coconut oil, the solution contained in a soft gelatin capsule and further comprising an antioxidant selected from the group consisting of butylated hydroxyanisole (BHA), butylated hydroxytoluene (BHT), vitamin E, and combinations thereof.

The composition of paragraph [0096], comprising a solid pharmaceutical preparation of an effective amount of the stabilized 1,25-dihydroxyvitamin $D_2$ composition, wherein the solid pharmaceutical preparation is in the form of a tablet, a capsule, a granule or a powder.

A method for purifying crude 1,25-dihydroxyvitamin $D_2$, comprising crystallizing 1,25-dihydroxyvitamin $D_2$ from a solvent system free of methyl formate.

The method of paragraph [00101], wherein the solvent system is further free of at least one of the following solvents selected from the group consisting of formate ester solvents, acetate ester solvents, lactate ester solvents, alcohol ester solvents, halogenated solvents, dimethylsulfoxide, dimethylformamide, and solvents capable of generating acid.

The method of paragraph [00102], wherein the solvent system is free of formate ester solvents, acetate ester solvents, lactate ester solvents, alcohol ester solvents, halogenated solvents, dimethylsulfoxide, dimethylformamide, and solvents capable of generating acid.

The method of paragraph [00101], comprising performing said crystallization as the final crystallization stage in a multi-stage crystallization purification.

The method of paragraph [00101], wherein the solvent system is an acetone/water mixture.

The method according to paragraph [00105], comprising
refluxing crude 1,25-dihydroxyvitamin $D_2$ with HPLC grade acetone;
filtering off solids;
adding a volume of 18.2 megaohm water to the acetone solution; and
reducing the temperature of the solution to crystallize 1,25-dihydroxyvitamin $D_2$.

The method according to paragraph [00105], further comprising washing the crystallized 1,25-dihydroxyvitamin $D_2$ with an acetone/water solution and drying the crystallized 1,25-dihydroxyvitamin $D_2$ to remove residual solvents.

The foregoing description is given for clearness of understanding only, and no unnecessary limitations should be understood therefrom, as modifications within the scope of the invention may be apparent to those having ordinary skill in the art.

Throughout the specification, where compositions are described as including components or materials, it is contemplated that the compositions can also consist essentially of, or consist of, any combination of the recited components or materials, unless described otherwise.

The practice of a method disclosed herein, and individual steps thereof, can be performed manually and/or with the aid of electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

All patents, publications and references cited herein are hereby fully incorporated by reference. In case of conflict between the present disclosure and incorporated patents, publications and references, the present disclosure should control.

What is claimed is:

1. A stabilized, crystalline 1,25-dihydroxyvitamin $D_2$ composition, characterized by:
    (a) being free of formate ester solvents;
    (b) comprising no more than 0.5% by weight of total residual solvents; and
    (c) wherein an initial purity of the composition is in a range of 98-100% as manufactured and a second purity is in a range of 98-100% after the composition is stored at 60° C. for a period of 24 hours, and wherein both the initial and the second purities are based on total area under the curve ("AUC") by a high performance liquid chromatography ("HPLC") assay.

2. The stabilized, crystalline 1,25-dihydroxyvitamin $D_2$ composition according to claim 1, comprising no more than 0.5% by weight of 1,25-dihydroxyprevitamin $D_2$ based on the total weight of the 1,25-dihydroxyvitamin $D_2$.

3. The stabilized, crystalline 1,25-dihydroxyvitamin $D_2$ composition according to claim 1, further being free of acids and free of at least one solvent selected from the group consisting of acetate ester solvents, lactate ester solvents, alcohol ester solvents, halogenated solvents, dimethylsulfoxide, dimethylformamide, and solvents capable of generating acid at elevated temperature or over time.

4. The stabilized, crystalline 1,25-dihydroxyvitamin $D_2$ composition according to claim 1, wherein each of the initial and second purities of the composition is in a range of 98.5-100% based on total AUC by HPLC assay.

5. The stabilized, crystalline 1,25-dihydroxyvitamin $D_2$ composition according to claim 2, wherein the initial purity is in a range of 98.5-100% as manufactured and a third purity in a range of 98.5-100% after the composition as manufactured is stored at −20° C. under argon for a period of 12 months, based on total AUC by a HPLC assay.

6. A pharmaceutical composition comprising an active component which is the stabilized, crystalline 1,25-dihydroxyvitamin $D_2$ composition of claim 1 and a pharmaceutically acceptable excipient.

7. The composition of claim 6, which is selected from the group consisting of a tablet, a soft gelatin capsule, a non-aqueous solution, and a non-aqueous suspension.

8. The composition of claim 6, in unit dosage form, having a content of active component of 0.1 µg to 25 µg.

9. The composition of claim 7, comprising a solution of an effective amount of the stabilized, crystalline 1,25-dihydroxyvitamin $D_2$ dissolved in fractionated coconut oil, the solution contained in a soft gelatin capsule and further comprising an antioxidant selected from the group consisting of butylated hydroxyanisole (BHA), butylated hydroxytoluene (BHT), vitamin E, and combinations thereof.

10. The composition of claim 6, comprising a solid pharmaceutical preparation of an effective amount of the stabilized, crystalline 1,25-dihydroxyvitamin $D_2$ composition, wherein the solid pharmaceutical preparation is in the form of a tablet, a capsule, a granule or a powder.

11. The stabilized, crystalline 1,25-dihydroxyvitamin $D_2$ composition of claim 1, wherein each of the initial and second purities is in a range of 99-100%, based on total AUC by a HPLC assay.

12. The stabilized, crystalline 1,25-dihydroxyvitamin $D_2$ composition according to claim 1, being free of acids and free of formate ester solvents, acetate ester solvents, lactate ester solvents, alcohol ester solvents, halogenated solvents, dimethylsulfoxide, dimethylformamide, and solvents capable of generating acid at elevated temperature or over time.

13. A stabilized 1,25-dihydroxyvitamin $D_2$ composition, characterized by:
    (a) being free of formate ester solvents;
    (b) having no more than 0.5% total residual solvents by weight;
    (c) comprising one or more of 1β,25-dihydroxyvitamin $D_2$, 5,6-trans-1,25-dihydroxyvitamin $D_2$, 1,25-dihydroxyprevitamin $D_2$, and 22-cis-1,25-dihydroxyvitamin $D_2$ present in a total amount up to 0.5%, based on total area under the curve ("AUC") by a high performance liquid chromatography ("HPLC") assay; and
    (d) comprising an initial amount of 1,25-dihydroxyvitamin $D_2$ as manufactured and a second amount of the 1,25-dihydroxyvitamin $D_2$ after the composition is stored at −20° C. under argon for a period of 12 months, wherein the initial and second amounts each are in a range of 98.5-100% purity based on AUC by HPLC assay, and the second amount is 99.5-100% of the initial amount.

14. A pharmaceutical formulation comprising an oil and a stabilized 1,25-dihydroxyvitamin $D_2$ composition according to claim 13 dissolved in the oil.

15. The formulation of claim 14, wherein the formulation is in a capsule.

16. The formulation of claim 15, wherein the formulation comprises an antioxidant.

17. A solid pharmaceutical formulation comprising a stabilized 1,25-dihydroxyvitamin $D_2$ composition according to claim 13 and one or more pharmaceutically acceptable excipients.

18. The formulation of claim 17, wherein the formulation is in the form of a tablet, a capsule, a granule, or a powder.

19. A stabilized, crystalline 1,25-dihydroxyvitamin $D_2$ composition, characterized by:

(a) being free of formate ester solvents;
(b) having no more than 0.5% total residual solvents as measured by a high performance liquid chromatography ("HPLC") assay;
(c) comprising no more than 0.5% of 1β,25-dihydroxyvitamin $D_2$, 5,6-trans 1,25-dihydroxyvitamin $D_2$, 22-cis-1,25-dihydroxyvitamin $D_2$, and 1,25-dihydroxyprevitamin $D_2$ as measured by the HPLC assay;
(c) having an initial amount of 1,25-dihydroxyvitamin $D_2$ as manufactured;
(f) having a second amount of the 1,25-dihydroxyvitamin $D_2$ after the composition is stored at −20° C. under argon for a period of 12 months; and
(g) wherein the initial and second amounts each are in a range of 98.5-100% purity as measured by the HPLC assay, and the second amount is 99.5-100% of the initial amount.

* * * * *